(12) United States Patent
Cohen et al.

(10) Patent No.: US 8,460,205 B2
(45) Date of Patent: Jun. 11, 2013

(54) FORCEPS AND COLLECTION ASSEMBLY WITH ACCOMPANYING MECHANISMS AND RELATED METHODS OF USE

(75) Inventors: Adam L. Cohen, Arlington, MA (US); John B. Golden, Norton, MA (US); Liem T. Vu, Needham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 13 days.

(21) Appl. No.: 13/306,647

(22) Filed: Nov. 29, 2011

(65) Prior Publication Data

US 2012/0137794 A1    Jun. 7, 2012

Related U.S. Application Data

(60) Continuation of application No. 12/461,262, filed on Aug. 5, 2009, now Pat. No. 8,083,686, which is a division of application No. 10/658,261, filed on Sep. 10, 2003, now Pat. No. 7,588,545.

(51) Int. Cl.
*A61B 10/06* (2006.01)
*A61B 17/32* (2006.01)

(52) U.S. Cl.
USPC .......................................... 600/564; 606/207

(58) Field of Classification Search
USPC .................. 606/207; 600/562–564
See application file for complete search history.

(56) References Cited

U.S. PATENT DOCUMENTS

| | | |
|---|---|---|
| 30,471 A | 10/1860 | Dudley |
| 1,609,014 A | 11/1926 | Dowd |
| 1,615,494 A | 1/1927 | Waring |
| 1,924,348 A | 8/1933 | Brown |
| 1,931,740 A | 10/1933 | Ryan |
| 2,115,298 A | 4/1938 | Brown |
| 2,131,780 A | 10/1938 | Storz |
| 2,258,287 A | 10/1941 | Grieshaber |
| 2,729,210 A | 1/1956 | Spencer |
| 2,751,908 A | 6/1956 | Wallace |
| 2,778,357 A | 1/1957 | Leibinger et al. |
| 3,590,808 A | 7/1971 | Muller |
| 3,683,892 A | 8/1972 | Harris |
| 3,844,272 A | 10/1974 | Banko |
| 3,889,657 A | 6/1975 | Baumgarten |
| 4,522,206 A | 6/1985 | Whipple et al. |
| 4,598,710 A | 7/1986 | Kleinberg et al. |
| 4,632,110 A | 12/1986 | Sanagi |
| 4,644,951 A | 2/1987 | Bays |
| 4,649,904 A | 3/1987 | Krauter et al. |
| 4,651,752 A | 3/1987 | Fuerst |

(Continued)

FOREIGN PATENT DOCUMENTS

| | | |
|---|---|---|
| DE | G 85 32 644.5 | 5/1986 |
| DE | 8712328 U1 | 3/1988 |

(Continued)

*Primary Examiner* — Brian Szmal
*Assistant Examiner* — Emily Lloyd
(74) *Attorney, Agent, or Firm* — Bookoff McAndrews, PLLC

(57) ABSTRACT

The invention includes a forceps and collection assembly for acquiring and storing a plurality of tissue samples in a single pass, and accompanying mechanisms for use with the forceps and collection assembly. The accompanying mechanisms include an endoscope working channel cap assembly configured to minimize compression of a pouch of the forceps and collection assembly as it traverses a seal of the cap assembly, and a flush adapter configured to be coupled to the pouch so as to assist in removing tissue samples in the pouch by flowing fluid through the pouch.

19 Claims, 10 Drawing Sheets

U.S. PATENT DOCUMENTS

| | | | |
|---|---|---|---|
| 4,651,753 A | 3/1987 | Lifton | |
| 4,656,999 A | 4/1987 | Storz | |
| 4,662,371 A | 5/1987 | Whipple et al. | |
| 4,669,471 A | 6/1987 | Hayashi | |
| 4,676,249 A | 6/1987 | Arenas | |
| 4,712,545 A | 12/1987 | Honkanen | |
| 4,721,116 A | 1/1988 | Schintgen et al. | |
| 4,763,668 A | 8/1988 | Macek et al. | |
| 4,763,669 A | 8/1988 | Jaeger | |
| 4,785,825 A | 11/1988 | Romaniuk et al. | |
| 4,815,460 A | 3/1989 | Porat et al. | |
| 4,815,476 A | 3/1989 | Clossick | |
| 4,817,630 A | 4/1989 | Schintgen et al. | |
| 4,880,015 A | 11/1989 | Nierman | |
| 4,887,612 A | 12/1989 | Esser et al. | |
| 4,889,118 A | 12/1989 | Schwiegerling | |
| 4,907,599 A | 3/1990 | Taylor | |
| 4,936,312 A | 6/1990 | Tsukagoshi | |
| 4,950,273 A | 8/1990 | Briggs | |
| 4,953,559 A | 9/1990 | Salerno | |
| 4,971,067 A | 11/1990 | Bolduc et al. | |
| 4,986,279 A | 1/1991 | O'Neill | |
| 4,986,825 A | 1/1991 | Bays et al. | |
| 4,994,024 A | 2/1991 | Falk | |
| 5,037,379 A | 8/1991 | Clayman et al. | |
| 5,052,402 A | 10/1991 | Bencini et al. | |
| 5,059,214 A | 10/1991 | Akopov et al. | |
| 5,074,867 A | 12/1991 | Wilk | |
| 5,082,000 A | 1/1992 | Picha et al. | |
| 5,085,659 A | 2/1992 | Rydell | |
| 5,147,371 A | 9/1992 | Washington et al. | |
| 5,148,813 A | 9/1992 | Bucalo | |
| 5,152,778 A | 10/1992 | Bales, Jr. et al. | |
| 5,161,542 A | 11/1992 | Palestrant | |
| 5,171,256 A | 12/1992 | Smith et al. | |
| 5,172,700 A | 12/1992 | Bencini et al. | |
| 5,176,687 A | 1/1993 | Hasson et al. | |
| 5,183,052 A | 2/1993 | Terwilliger | |
| 5,183,054 A | 2/1993 | Burkholder et al. | |
| 5,188,118 A | 2/1993 | Terwilliger | |
| 5,190,542 A | 3/1993 | Nakao et al. | |
| 5,190,555 A | 3/1993 | Wetter et al. | |
| 5,192,284 A | 3/1993 | Pleatman | |
| 5,192,286 A | 3/1993 | Phan et al. | |
| 5,195,533 A | 3/1993 | Chin et al. | |
| 5,197,968 A | 3/1993 | Clement | |
| 5,201,740 A | 4/1993 | Nakao et al. | |
| 5,217,458 A | 6/1993 | Parins | |
| 5,238,002 A | 8/1993 | Devlin et al. | |
| 5,241,968 A | 9/1993 | Slater | |
| 5,249,582 A | 10/1993 | Taylor | |
| 5,251,641 A | 10/1993 | Xavier | |
| 5,263,967 A | 11/1993 | Lyons, III et al. | |
| 5,267,572 A | 12/1993 | Bucalo | |
| 5,285,795 A | 2/1994 | Ryan et al. | |
| 5,300,087 A | 4/1994 | Knoepfler | |
| 5,316,013 A | 5/1994 | Striebel et al. | |
| 5,330,502 A | 7/1994 | Hassler et al. | |
| 5,341,815 A | 8/1994 | Cofone et al. | |
| 5,342,389 A | 8/1994 | Haber et al. | |
| 5,348,023 A | 9/1994 | McLucas | |
| 5,352,184 A | 10/1994 | Goldberg et al. | |
| 5,354,303 A | 10/1994 | Spaeth et al. | |
| 5,357,946 A | 10/1994 | Kee et al. | |
| 5,366,467 A | 11/1994 | Lynch et al. | |
| 5,368,597 A | 11/1994 | Pagedas | |
| 5,373,854 A | 12/1994 | Kolozsi | |
| 5,374,227 A | 12/1994 | Webb | |
| 5,374,277 A | 12/1994 | Hassler | |
| 5,383,888 A | 1/1995 | Zvenyatsky et al. | |
| 5,385,570 A | 1/1995 | Chin et al. | |
| 5,396,900 A | 3/1995 | Slater et al. | |
| 5,419,220 A | 5/1995 | Cox | |
| 5,423,854 A | 6/1995 | Martin et al. | |
| 5,449,001 A | 9/1995 | Terwilliger | |
| 5,465,731 A | 11/1995 | Bell et al. | |
| 5,471,992 A | 12/1995 | Banik et al. | |
| 5,476,099 A | 12/1995 | Robinson et al. | |
| 5,482,054 A | 1/1996 | Slater et al. | |
| 5,511,556 A | 4/1996 | De Santis | |
| 5,535,754 A | 7/1996 | Doherty | |
| 5,538,008 A | 7/1996 | Crowe | |
| 5,542,432 A | 8/1996 | Slater et al. | |
| 5,558,100 A | 9/1996 | Cox | |
| 5,560,373 A | 10/1996 | De Santis | |
| 5,562,102 A | 10/1996 | Taylor | |
| 5,564,436 A | 10/1996 | Hakky et al. | |
| 5,571,129 A | 11/1996 | Porter | |
| 5,573,008 A | 11/1996 | Robinson et al. | |
| 5,595,185 A | 1/1997 | Erlich | |
| 5,601,585 A | 2/1997 | Banik et al. | |
| 5,636,639 A | 6/1997 | Turturro et al. | |
| 5,638,827 A | 6/1997 | Palmer et al. | |
| 5,643,283 A | 7/1997 | Younker | |
| 5,643,307 A | 7/1997 | Turkel et al. | |
| 5,645,075 A | 7/1997 | Palmer et al. | |
| 5,647,372 A | 7/1997 | Tovey et al. | |
| 5,653,713 A | 8/1997 | Michelson | |
| 5,662,671 A | 9/1997 | Barbut et al. | |
| 5,669,394 A | 9/1997 | Bergey et al. | |
| 5,681,324 A | 10/1997 | Kammerer et al. | |
| 5,681,348 A | 10/1997 | Sato | |
| 5,683,359 A | 11/1997 | Farkas et al. | |
| 5,683,388 A | 11/1997 | Slater | |
| 5,683,413 A | 11/1997 | Miyagi | |
| 5,707,392 A | 1/1998 | Kortenbach | |
| 5,720,754 A | 2/1998 | Middleman et al. | |
| 5,735,289 A | 4/1998 | Pfeffer et al. | |
| 5,746,216 A | 5/1998 | Turturro et al. | |
| 5,746,740 A | 5/1998 | Nicholas | |
| 5,759,187 A | 6/1998 | Nakao et al. | |
| 5,762,069 A | 6/1998 | Kelleher et al. | |
| 5,762,070 A | 6/1998 | Nagamatsu | |
| 5,762,613 A | 6/1998 | Sutton et al. | |
| 5,766,177 A | 6/1998 | Lucas-Dean et al. | |
| 5,775,333 A | 7/1998 | Burbank et al. | |
| 5,776,075 A | 7/1998 | Palmer | |
| 5,779,646 A | 7/1998 | Koblish et al. | |
| 5,779,648 A | 7/1998 | Banik et al. | |
| 5,779,716 A | 7/1998 | Cano et al. | |
| 5,795,308 A | 8/1998 | Russin | |
| 5,797,957 A | 8/1998 | Palmer et al. | |
| 5,807,276 A | 9/1998 | Russin | |
| 5,807,277 A | 9/1998 | Swaim | |
| 5,810,744 A | 9/1998 | Chu et al. | |
| 5,810,876 A | 9/1998 | Kelleher | |
| 5,820,630 A | 10/1998 | Lind | |
| 5,823,971 A | 10/1998 | Robinson et al. | |
| 5,840,043 A | 11/1998 | Palmer et al. | |
| 5,840,044 A | 11/1998 | Dassa et al. | |
| 5,843,000 A | 12/1998 | Nishioka et al. | |
| 5,846,248 A | 12/1998 | Chu et al. | |
| 5,848,978 A | 12/1998 | Cecchi | |
| 5,853,374 A | 12/1998 | Hart et al. | |
| 5,871,453 A | 2/1999 | Banik et al. | |
| 5,893,876 A | 4/1999 | Turkel et al. | |
| 5,895,361 A | 4/1999 | Turturro | |
| 5,897,507 A | 4/1999 | Kortenbach et al. | |
| 5,906,621 A | 5/1999 | Secrest et al. | |
| 5,908,437 A | 6/1999 | Asano et al. | |
| 5,919,206 A | 7/1999 | Gengler et al. | |
| 5,928,161 A | 7/1999 | Krulevitch et al. | |
| 5,928,164 A | 7/1999 | Burbank et al. | |
| 5,944,673 A | 8/1999 | Gregoire et al. | |
| 5,957,932 A | 9/1999 | Bates et al. | |
| 5,961,534 A | 10/1999 | Banik et al. | |
| 5,964,716 A | 10/1999 | Gregoire et al. | |
| 5,967,997 A | 10/1999 | Turturro et al. | |
| 5,971,940 A | 10/1999 | Baker et al. | |
| 5,980,468 A | 11/1999 | Zimmon | |
| 6,007,546 A | 12/1999 | Snow et al. | |
| 6,010,512 A | 1/2000 | Chu et al. | |
| 6,013,095 A | 1/2000 | Ouchi | |
| 6,019,733 A | 2/2000 | Farascioni | |
| 6,019,758 A | 2/2000 | Slater | |
| 6,019,770 A | 2/2000 | Christoudias | |
| 6,022,362 A | 2/2000 | Lee et al. | |

| | | |
|---|---|---|
| 6,036,698 A | 3/2000 | Fawzi et al. |
| RE36,666 E | 4/2000 | Honkanen et al. |
| 6,050,955 A | 4/2000 | Bryan et al. |
| 6,053,877 A | 4/2000 | Banik et al. |
| 6,059,793 A | 5/2000 | Pagedas |
| 6,068,603 A | 5/2000 | Suzuki |
| 6,071,233 A | 6/2000 | Ishikawa et al. |
| 6,071,248 A | 6/2000 | Zimmon |
| 6,074,408 A | 6/2000 | Freeman |
| 6,077,230 A | 6/2000 | Gregoire et al. |
| 6,083,150 A | 7/2000 | Aznoian et al. |
| 6,083,240 A | 7/2000 | Ouchi |
| 6,093,195 A | 7/2000 | Ouchi |
| 6,099,483 A | 8/2000 | Palmer et al. |
| 6,099,534 A | 8/2000 | Bates et al. |
| 6,106,553 A | 8/2000 | Feingold |
| 6,110,127 A | 8/2000 | Suzuki |
| 6,123,678 A | 9/2000 | Palmer et al. |
| 6,129,683 A | 10/2000 | Sutton et al. |
| 6,139,508 A | 10/2000 | Simpson et al. |
| 6,142,955 A | 11/2000 | Farascioni et al. |
| 6,142,956 A | 11/2000 | Kortenbach et al. |
| 6,142,957 A | 11/2000 | Diamond et al. |
| 6,149,607 A | 11/2000 | Simpson et al. |
| 6,155,988 A | 12/2000 | Peters |
| 6,159,162 A | 12/2000 | Kostylev et al. |
| 6,168,603 B1 | 1/2001 | Leslie et al. |
| 6,171,315 B1 | 1/2001 | Chu et al. |
| 6,174,292 B1 | 1/2001 | Kortenbach et al. |
| 6,174,318 B1 | 1/2001 | Bates et al. |
| 6,183,482 B1 | 2/2001 | Bates et al. |
| 6,190,399 B1 | 2/2001 | Palmer et al. |
| 6,193,671 B1 | 2/2001 | Turturro et al. |
| 6,206,904 B1 | 3/2001 | Ouchi |
| 6,224,612 B1 | 5/2001 | Bates et al. |
| 6,228,095 B1 | 5/2001 | Dennis |
| 6,231,522 B1 | 5/2001 | Voegele et al. |
| 6,241,687 B1 | 6/2001 | Voegele et al. |
| 6,248,081 B1 | 6/2001 | Nishtalas et al. |
| 6,258,102 B1 | 7/2001 | Pagedas |
| 6,264,618 B1 | 7/2001 | Landi et al. |
| 6,264,663 B1 | 7/2001 | Cano |
| 6,273,860 B1 | 8/2001 | Kostylev et al. |
| 6,273,861 B1 | 8/2001 | Bates et al. |
| 6,280,398 B1 | 8/2001 | Ritchart et al. |
| 6,280,451 B1 | 8/2001 | Bates et al. |
| 6,283,924 B1 | 9/2001 | Ouchi |
| 6,299,630 B1 | 10/2001 | Yamamoto |
| 6,309,404 B1 | 10/2001 | Krzyzanowski |
| 6,322,522 B1 | 11/2001 | Zimmon |
| 6,328,701 B1 | 12/2001 | Terwilliger |
| 6,331,165 B1 | 12/2001 | Turturro et al. |
| 6,350,266 B1 | 2/2002 | White et al. |
| 6,368,290 B1 | 4/2002 | Baska |
| 6,375,661 B2 | 4/2002 | Chu et al. |
| 6,378,351 B1 | 4/2002 | Ouchi et al. |
| 6,383,196 B1 | 5/2002 | Leslie et al. |
| 6,383,197 B1 | 5/2002 | Conlon et al. |
| 6,387,102 B2 | 5/2002 | Pagedas |
| 6,409,678 B1 | 6/2002 | Ouchi |
| 6,409,733 B1 | 6/2002 | Conlon et al. |
| 6,419,640 B1 | 7/2002 | Taylor |
| 6,419,679 B1 | 7/2002 | Dhindsa |
| 6,425,910 B1 | 7/2002 | Hugueny et al. |
| 6,427,509 B1 | 8/2002 | Ouchi et al. |
| 6,432,064 B1 | 8/2002 | Hibner et al. |
| 6,436,054 B1 | 8/2002 | Viola et al. |
| 6,440,085 B1 | 8/2002 | Krzyzanowski |
| 6,443,909 B1 | 9/2002 | Ouchi |
| 6,454,727 B1 | 9/2002 | Burbank et al. |
| 6,461,310 B1 | 10/2002 | Palmer et al. |
| 6,468,227 B2 | 10/2002 | Zimmon |
| 6,485,436 B1 | 11/2002 | Truckai et al. |
| 6,488,636 B2 | 12/2002 | Bryan et al. |
| 6,494,885 B1 | 12/2002 | Dhindsa |
| 6,514,197 B1 | 2/2003 | Ouchi et al. |
| 6,514,269 B2 | 2/2003 | Yamamoto |
| 6,517,498 B1 | 2/2003 | Burbank et al. |
| 6,520,968 B2 | 2/2003 | Bates et al. |
| 6,527,781 B2 | 3/2003 | Bates et al. |
| 6,530,891 B2 | 3/2003 | Miller |
| 6,544,194 B1 | 4/2003 | Kortenbach et al. |
| 6,551,254 B2 | 4/2003 | Nishtalas et al. |
| 6,554,850 B1 | 4/2003 | Ouchi et al. |
| 6,561,988 B1 | 5/2003 | Turturro et al. |
| 6,565,591 B2 | 5/2003 | Brady et al. |
| 6,575,977 B1 | 6/2003 | Michelson |
| 6,589,252 B2 | 7/2003 | McGuckin |
| 6,607,227 B1 | 8/2003 | Morton |
| 6,613,068 B2 | 9/2003 | Ouchi |
| 6,620,111 B2 | 9/2003 | Stephens et al. |
| 6,626,915 B2 | 9/2003 | Leveillee |
| 6,632,182 B1 | 10/2003 | Treat |
| 6,673,092 B1 | 1/2004 | Bacher |
| 6,685,723 B1 | 2/2004 | Ouchi et al. |
| 6,689,122 B2 | 2/2004 | Yamamoto |
| 6,695,791 B2 | 2/2004 | Gonzalez |
| 6,709,445 B2 | 3/2004 | Boebel et al. |
| 6,736,781 B2 | 5/2004 | Lee |
| 6,740,106 B2 | 5/2004 | Kobayashi et al. |
| 6,743,228 B2 | 6/2004 | Lee et al. |
| 6,752,822 B2 | 6/2004 | Jespersen |
| 6,792,663 B2 | 9/2004 | Krzyzanowski |
| 6,805,699 B2 | 10/2004 | Shimm |
| 6,808,491 B2 | 10/2004 | Kortenbach et al. |
| 7,118,586 B1 | 10/2006 | Paternuosto |
| 2001/0000348 A1 | 4/2001 | Chu et al. |
| 2001/0009978 A1 | 7/2001 | Krueger et al. |
| 2001/0047124 A1 | 11/2001 | Yamamoto |
| 2001/0056248 A1 | 12/2001 | Zimmon |
| 2002/0013595 A1 | 1/2002 | Yamamoto |
| 2002/0022850 A1 | 2/2002 | McGuckin |
| 2002/0029006 A1 | 3/2002 | Turturro et al. |
| 2002/0065474 A1 | 5/2002 | Viola et al. |
| 2002/0068944 A1 | 6/2002 | White et al. |
| 2002/0095100 A1 | 7/2002 | Lee et al. |
| 2002/0111564 A1 | 8/2002 | Burbank et al. |
| 2002/0120211 A1 | 8/2002 | Wardle et al. |
| 2002/0143270 A1 | 10/2002 | Miller |
| 2002/0156395 A1 | 10/2002 | Stephens et al. |
| 2002/0188220 A1 | 12/2002 | Krzyzanowski |
| 2002/0193705 A1 | 12/2002 | Burbank et al. |
| 2002/0198466 A1 | 12/2002 | Alberico |
| 2003/0040681 A1 | 2/2003 | Ng et al. |
| 2003/0073928 A1 | 4/2003 | Kortenbach et al. |
| 2003/0097147 A1 | 5/2003 | Prestel |
| 2003/0105402 A1 | 6/2003 | Lee |
| 2003/0120281 A1 | 6/2003 | Bates et al. |
| 2003/0125639 A1 | 7/2003 | Fisher et al. |
| 2003/0163129 A1 | 8/2003 | Lee et al. |
| 2003/0191413 A1 | 10/2003 | Damarati |
| 2003/0191464 A1 | 10/2003 | Kidooka |
| 2003/0212342 A1 | 11/2003 | Rudnick et al. |
| 2003/0229292 A1 | 12/2003 | Hibner et al. |
| 2003/0229293 A1 | 12/2003 | Hibner et al. |
| 2004/0015165 A1 | 1/2004 | Kidooka |
| 2004/0024333 A1 | 2/2004 | Brown |
| 2004/0034310 A1 | 2/2004 | McAlister et al. |
| 2004/0059345 A1 | 3/2004 | Nakao et al. |
| 2004/0068291 A1 | 4/2004 | Suzuki |
| 2004/0087872 A1 | 5/2004 | Anderson et al. |
| 2004/0087979 A1 | 5/2004 | Field et al. |
| 2004/0092967 A1 | 5/2004 | Sancoff et al. |
| 2004/0097829 A1 | 5/2004 | McRury et al. |
| 2004/0138587 A1 | 7/2004 | Lyons |
| 2004/0199159 A1 | 10/2004 | Lee et al. |
| 2004/0220496 A1 | 11/2004 | Gonzalez |
| 2004/0254592 A1 | 12/2004 | DiCarlo et al. |

FOREIGN PATENT DOCUMENTS

| | | |
|---|---|---|
| DE | 8814560 U1 | 3/1989 |
| DE | 3920706 A1 | 1/1991 |
| DE | 4006673 A1 | 9/1991 |
| DE | 9211834 U1 | 4/1993 |
| DE | 68913909 T2 | 10/1994 |
| DE | 695 27 152 T2 | 6/1996 |
| DE | 29614931 U1 | 3/1997 |
| DE | 69310072 T2 | 11/1997 |

| | | | | | | |
|---|---|---|---|---|---|---|
| DE | 69404526 T2 | 12/1997 | | JP | H11-076244 A | 3/1999 |
| DE | 69319668 T2 | 12/1998 | | JP | 3220164 B2 | 8/1999 |
| DE | 10018674 A1 | 11/2000 | | JP | H11-509132 T2 | 8/1999 |
| DE | 10048369 A1 | 4/2001 | | JP | H11-509459 T2 | 8/1999 |
| DE | 10048369 C2 | 4/2001 | | JP | H11-239582 A | 9/1999 |
| DE | 10051651 A1 | 4/2001 | | JP | 2000-279418 A | 10/2000 |
| DE | 10056946 A1 | 5/2001 | | JP | 2000-296131 A | 10/2000 |
| DE | 10128553 A1 | 1/2002 | | JP | 2001-095808 A | 4/2001 |
| DE | 10123848 A1 | 2/2002 | | JP | 2001-112763 A | 4/2001 |
| DE | 10156313 A1 | 6/2003 | | JP | 2001-137998 A | 5/2001 |
| DE | 10316134 A1 | 10/2003 | | JP | 3190029 B2 | 7/2001 |
| DE | 10332613 A1 | 2/2004 | | JP | 2001-517468 A | 10/2001 |
| EP | 0 207 829 A1 | 1/1987 | | JP | 3220165 B2 | 10/2001 |
| EP | 0 207 830 A1 | 1/1987 | | JP | 2001-321386 A | 11/2001 |
| EP | 0 279 358 A2 | 8/1988 | | JP | 2002-011014 A | 1/2002 |
| EP | 0 279 358 B1 | 8/1988 | | JP | 2002-065598 A | 3/2002 |
| EP | 0 380 874 A1 | 8/1990 | | JP | 2003-093393 A | 4/2003 |
| EP | 0 367 818 B1 | 3/1994 | | JP | 2004-000424 A | 1/2004 |
| EP | 0 585 921 A1 | 3/1994 | | JP | 2004-049330 A | 2/2004 |
| EP | 0 593 929 A1 | 4/1994 | | WO | WO 89/10093 A1 | 11/1989 |
| EP | 0 592 243 B1 | 4/1997 | | WO | WO 90/01297 A1 | 2/1990 |
| EP | 0 621 009 B1 | 7/1997 | | WO | WO 94/13215 | 6/1994 |
| EP | 0 573 817 B1 | 7/1998 | | WO | WO 94/26172 A1 | 11/1994 |
| EP | 0 798 982 B1 | 6/2002 | | WO | WO 94/26181 A1 | 11/1994 |
| EP | 1 240 870 A2 | 9/2002 | | WO | WO 95/20914 A1 | 8/1995 |
| EP | 1 252 863 A1 | 10/2002 | | WO | WO 96/19144 A1 | 6/1996 |
| EP | 1 312 313 A1 | 5/2003 | | WO | WO 96/24289 A2 | 8/1996 |
| EP | 1 348 378 A1 | 10/2003 | | WO | WO 97/41776 A1 | 11/1997 |
| EP | 1 371 332 A1 | 12/2003 | | WO | WO 97/41777 A1 | 11/1997 |
| EP | 1 001 706 B1 | 3/2004 | | WO | WO 98/06336 A1 | 2/1998 |
| JP | S62-049838 A | 3/1987 | | WO | WO 98/35615 A1 | 8/1998 |
| JP | H09-215747 A | 8/1987 | | WO | WO 99/07287 A1 | 2/1999 |
| JP | S62-176438 A | 8/1987 | | WO | WO 99/15073 A1 | 4/1999 |
| JP | H03-139340 A | 6/1991 | | WO | WO 99/20096 A2 | 4/1999 |
| JP | H04-307050 A | 10/1992 | | WO | WO 99/53851 A1 | 10/1999 |
| JP | H05-220157 A | 8/1993 | | WO | WO 00/01304 A1 | 1/2000 |
| JP | H05-237120 A | 9/1993 | | WO | WO 00/07502 A1 | 2/2000 |
| JP | H06-030942 A | 2/1994 | | WO | WO 00/33743 | 6/2000 |
| JP | H06-114063 A | 4/1994 | | WO | WO 00/54658 A1 | 9/2000 |
| JP | H06-189966 A | 7/1994 | | WO | WO 01/30242 A1 | 5/2001 |
| JP | H06-197906 A | 7/1994 | | WO | WO 02/062226 A1 | 8/2002 |
| JP | H08-206120 A | 8/1996 | | WO | WO 02/062227 A1 | 8/2002 |
| JP | H08-224242 A | 9/1996 | | WO | WO 03/022157 A2 | 3/2003 |
| JP | H09-508561 T2 | 9/1997 | | WO | WO 03/024300 A2 | 3/2003 |
| JP | H09-276282 A | 10/1997 | | WO | WO 03/028557 A1 | 4/2003 |
| JP | 10-099342 | 4/1998 | | WO | WO 03/082119 A1 | 10/2003 |
| JP | H10-137246 A | 5/1998 | | WO | WO 03/082122 A1 | 10/2003 |
| JP | H10-137250 A | 5/1998 | | WO | WO 2004/010874 A1 | 2/2004 |
| JP | H10-137251 A | 5/1998 | | | | |

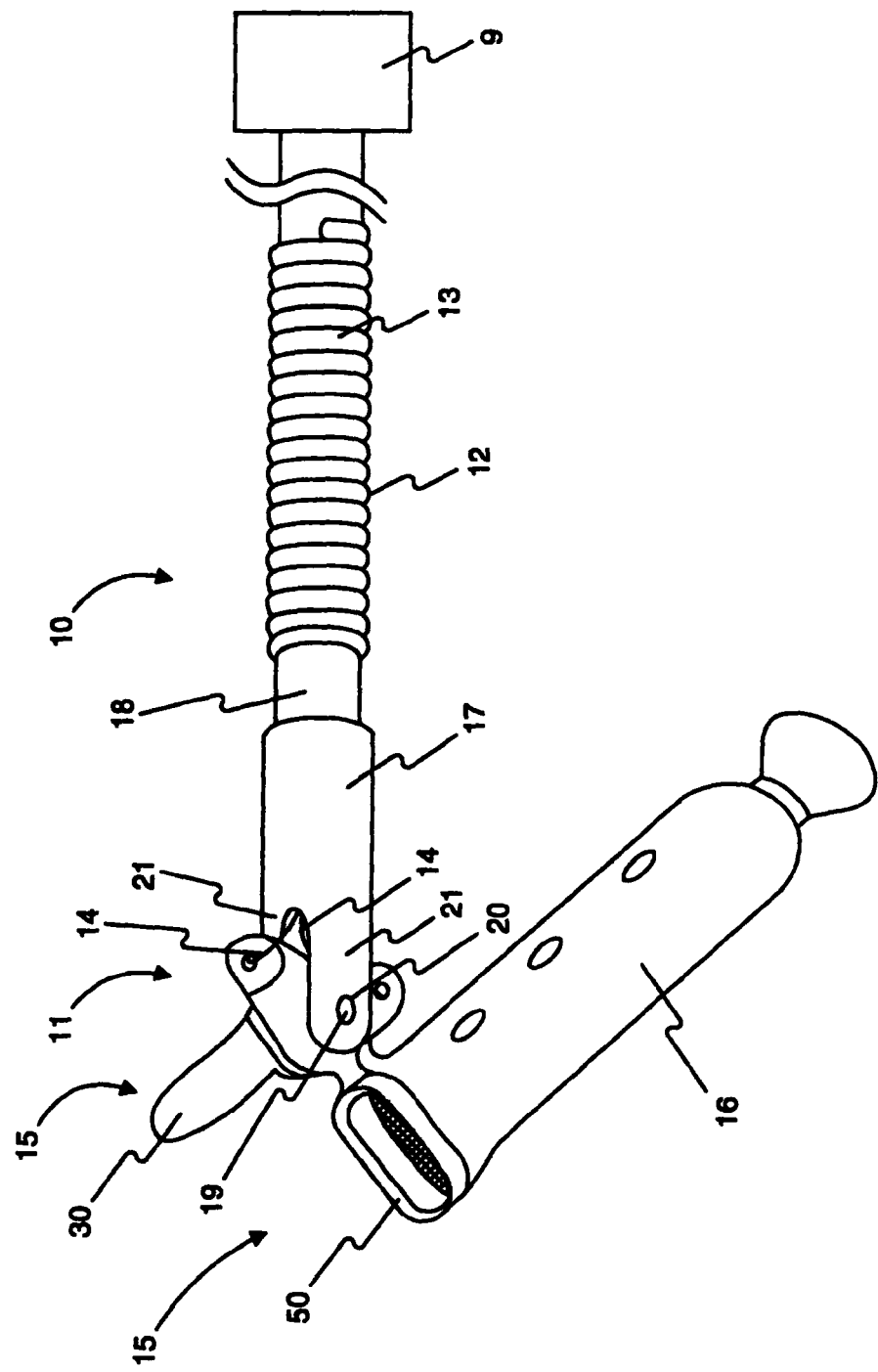

FORCEPS AND COLLECTION ASSEMBLY WITH ACCOMPANYING MECHANISMS AND RELATED METHODS OF USE

CROSS-REFERENCE TO RELATED APPLICATIONS

This application is a continuation of application Ser. No. 12/461,262, filed Aug. 5, 2009 now U.S. Pat. No. 8,083,686, which is a divisional of application Ser. No. 10/658,261, filed Sep. 10, 2003 now U.S. Pat. No. 7,588,545, all of which are relied upon and incorporated herein by reference.

FIELD OF THE INVENTION

The invention relates to a forceps and collection assembly having accompanying mechanisms and their related methods of use. More specifically, the invention relates to a forceps for obtaining and collecting multiple samples in a collection assembly, such as a pouch. The accompanying mechanisms include a flush adapter to aid in removal of samples from the collection assembly and, when used in a medical procedure such as an endoscopic biopsy procedure, a working channel cap to aid in insertion and removal of the forceps and collection assembly from an endoscope channel.

BACKGROUND OF THE INVENTION

Irritable bowel disease, Crohn's disease, and Barrett's esophagus are just some of the gastrointestinal diseases that often require biopsy or tissue samples to be taken from the gastrointestinal tract. Often, a large number of biopsy samples must be taken from various locations in the gastrointestinal tract in order to properly diagnose the disease.

Various current biopsy forceps, however, are only designed to take one or two samples in a single pass. Thus, during some procedures that routinely require as many as twenty or more samples, the forceps must be advanced into and retracted out of the gastrointestinal tract numerous times. Such advancing and retracting of the forceps is time consuming, can cause trauma to the surrounding tissue, and can create sterility issues. Accordingly, a device that minimizes the number of advancements and retractions of the forceps by acquiring and storing multiple biopsy samples in a single pass is desirable. In addition, once multiple samples have been obtained, a method and device for sample removal that overcomes, for example, the tissue sticking to or otherwise being lodged within the device, is needed. Moreover, a device is needed that will insert into and out of a working channel of an endoscope without losing the samples or compressing the samples, damaging their integrity and causing a loss in diagnostic quality.

It is accordingly an object of the invention to have a forceps and collection assembly that facilitate the collection and storage of multiple biopsy samples, and accompanying mechanisms that facilitate the removal of the biopsy samples from the pouch while allowing them to maintain their integrity.

SUMMARY OF THE INVENTION

In accordance with the invention, an embodiment of the invention includes a device for storing a plurality of tissue samples having an elongate container with a cavity for storing a plurality of tissue samples, an open top, and an open bottom in flow communication with the open top. The device also has a cutting portion coupled to the open top and configured to cut the plurality of tissue samples that deposit in the cavity through the open top. A portion of the elongate container adjacent the open bottom has a restriction smaller than the open bottom to prevent the plurality of tissue samples from exiting the container via the open bottom.

According to another aspect of the invention, an embodiment of the invention a device for storing a plurality of tissue samples having an elongate container with a cavity for storing a plurality of tissue samples, an open top, and an open bottom in flow communication with the open top. The open top and the open bottom are aligned with a longitudinal axis of the cavity. The device also has a cutting portion coupled to the open top and configured to cut the plurality of tissue samples that deposit in the cavity through the open top. A portion of the elongate container adjacent to the open bottom is configured to prevent the plurality of tissue samples from exiting the container via the open bottom.

According to yet another aspect of the invention, an embodiment of the invention includes an endoscope working channel cap assembly for coupling to an existing seal. The cap assembly includes an interface configured to be coupled to a proximal end of a working channel of an endoscope, an introducer extending from the interface and configured to be advanced through the existing seal and hold open the existing seal, and a seal portion connected to the interface. The seal portion includes a seal disposed therein and configured to prevent flow communication across the seal.

According to still another aspect of the invention, an embodiment of the invention includes a flushing device having an elongate member defining a receiving cavity, an open top, and an open bottom. The flushing device also includes a connector proximate the open bottom and configured to provide a fluid tight connection with a source of fluid, and a nozzle within the elongate member between the open bottom and the receiving cavity. The open bottom is in flow communication with the open top via the nozzle and the receiving cavity.

According to a further aspect of the invention, an embodiment of the invention includes an endoscopic instrument having a proximal handle coupled to a distal end effector assembly via an elongate member. The distal end effector assembly includes an upper jaw, a lower jaw rotatable relative to the upper jaw, and a collection device coupled to the lower jaw. The collection device includes an elongate container having a cavity for storing a plurality of tissue samples, an open top, and an open bottom in flow communication with the open top. The upper jaw and the lower jaw are configured to cut the plurality of tissue samples that deposit in the cavity through the open top, and a portion of the elongate container adjacent the open bottom has a restriction smaller than the open bottom to prevent the plurality of tissue samples from exiting the container via the open bottom.

According to a still further aspect of the invention, an embodiment of the invention includes a method of acquiring a plurality of tissue samples. The method includes using a device to cut a first tissue sample from an internal tissue tract of a patient and storing the first tissue sample in a container disposed within the internal tissue tract. The method also includes using the device to cut at least one additional tissue sample from the internal tissue tract without removing the device from the patient. The method further includes storing the at least one additional tissue sample in the container disposed within the internal tissue tract. The container has a cavity for storing the first and at least one additional tissue sample, an open top, and an open in flow communication with the open top. A portion of the container adjacent the open bottom has a restriction smaller than the open bottom to prevent the first and additional multiple tissue samples from exiting the container via the open bottom.

According to a yet further aspect of the invention, an embodiment of the invention includes a method of removing tissue samples from a container. The method includes providing a container having a cavity with tissue samples, an open top, and an open bottom in flow communication with the open top. A portion of the container adjacent the open bottom has a restriction smaller than the open bottom to prevent the tissue samples from exiting the container via the open bottom. The method also includes delivering fluid through the open bottom to flush the tissue samples out of the cavity via the open top.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 1 is a perspective view of a forceps and collection assembly according to an embodiment of the present invention.

Reference will now be made in detail to the present exemplary embodiments of the invention illustrated in the accompanying drawings. Wherever possible, the same reference numbers will be used throughout the drawings to refer to the same or like parts.

Figure 2A:
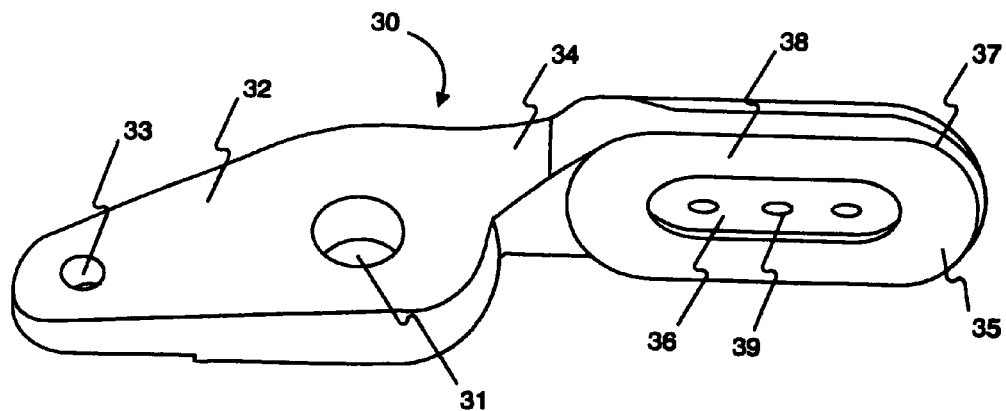
FIG. 2A is a perspective view of an upper jaw of the forceps and collection assembly of FIG. 1.

In the various embodiments, the invention relates to a forceps and collection assembly for obtaining and storing multiple tissue samples. The invention also related to various mechanisms to work in combination with such a forceps. For example, embodiments of the invention include an endoscope working channel cap configured to aid in insertion and removal of the forceps and collection assembly and minimize compression of the collection assembly and its stored samples, to maintain the integrity of those samples. Another mechanism for use in combination with the forceps and collection assembly includes a flush adapter configured to assist in the removal of the biopsy samples from the collection assembly.

In embodiments that use the forceps and collection assembly in an endoscopic medical procedure, the forceps and collection assembly can be advanced through a working channel cap that has a seal specifically designed for use with the forceps and collection assembly, down the working channel of an endoscope, and into a tissue tract. When proximate tissue sites, the forceps and collection assembly can take and store multiple biopsy samples, and then be retracted from the tissue tract through the working channel of the endoscope through the cap with the seal specifically designed to assist in both keeping the biopsy samples in the collection assembly, for example a pouch, and maintaining the diagnostic integrity of the biopsy samples. Once the forceps and collection assembly has been retracted from the body, the collection assembly is placed on a flush adapter configured to assist in efficiently removing the biopsy samples from the collection assembly without damaging the samples.

An embodiment of a forceps and collection assembly is depicted in FIG. 1. The forceps and collection assembly 10 includes an elongate tubular member 12 that is connected to an endoscopic actuator assembly 9 (i.e. a handle portion) at the proximal end of the assembly 10 and an end effector assembly 11 at a distal end of assembly 10. The endoscopic actuator assembly 9 is shown schematically in FIG. 1 as simply a box, as assembly 9 may be any suitable handle known in the art that controls the actuation of the distal jaw assembly and/or forceps. Tubular member 12 includes a flexible helical coil 13 that may include a covering. Any alternative elongate member having sufficient flexibility to traverse tortuous anatomy may be used to connect the proximal actuator assembly 9 to the distal end effector assembly 11.

The main components of end effector assembly 11 include a clevis 17, jaws 15, and a collection assembly in the form of a pouch 16. At its distal end 18, tubular member 12 is connected to jaws 15 and pouch 16 via clevis 17. The distal end of clevis 17 has a generally U-shaped configuration with a pivot pin 19 running between pivot holes 20 on opposing pivot arms 21 of the clevis 17. The center of the clevis 17 is hollow and configured to receive pull wires 14 used to actuate the jaws 15 located between the pivot arms 21 of the clevis 17. The pull wires 14 connect to jaws 15 and extend through clevis 17 and elongate member 12 to the proximal actuation handle 9.

Figure 2B:
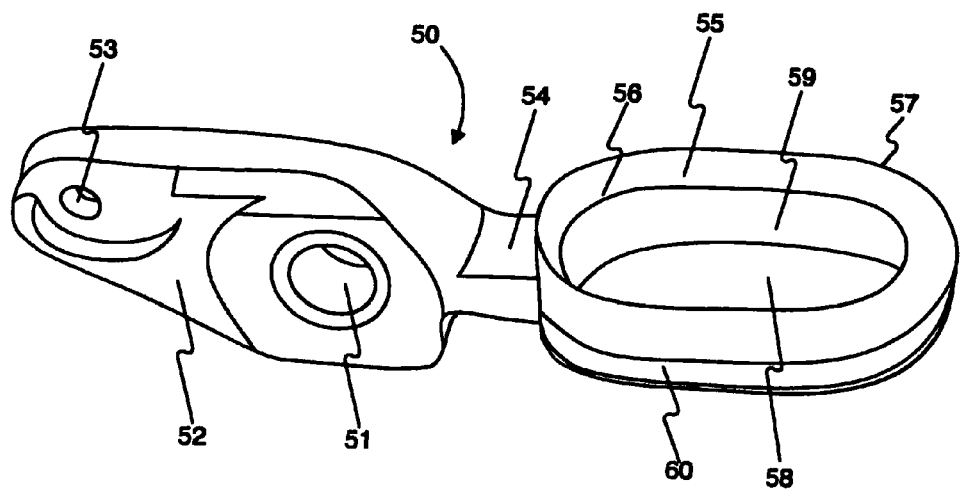
FIG. 2B is a perspective view of a lower jaw of the forceps and collection assembly of FIG. 1.

An embodiment of jaws 15 is depicted in FIGS. 2A-2B. The jaws 15 includes an upper jaw 30 and a lower jaw 50. The upper jaw 30 and lower jaw 50 each have pivot bores 31, 51 on the central part of their respective tang portions 32, 52 that are configured to accommodate the pivot pin 19 of the clevis 17 such that the upper jaw 30 and lower jaw 50 can rotate about the pivot pin 19 with respect to each other. Both the upper jaw 30 and lower jaw 50 have tang portions 32, 52 with pull wire holes 33, 53 on their proximal ends configured to receive and retain actuating pull wires 14 from the proximal actuation handle 9. Both the upper jaw 30 and lower jaw 50 also have central bridging portions 34, 54 that connect their respective proximal tang portions 32, 52 to distal cutting portions 35, 55. The upper jaw 30 and lower jaw 50 are both made out of a biocompatible metal suitable for accommodating and retaining sharp cutting edges 37, 57, or other material of sufficient strength (e.g. plastic ceramic composite). The cutting portions 35, 55 of the upper jaw 30 and lower jaw 50 are configured to be opposable and match up with each other when brought together.

The cutting portion 35 of the upper jaw 30 includes a straight cutting edge 37 around substantially the outer edge of the bottom part 36 of the cutting portion 35. Substantially adjacent to the inner portion of the straight cutting edge 37 of the upper jaw 30 is an oval protrusion 38. The oval protrusion 38 is for pushing samples into the pouch 16 connected to the lower jaw 50 once the tissue sample has been cut from the tissue tract. Substantially adjacent to the inner portion of the oval protrusion 38 on the bottom part 36 is a flat portion that has ventilating holes 39. The ventilating holes 39 are to assist in preventing biopsy samples from being stuck on the bottom portion 36 of the cutting portion 35 by minimizing the surface area that samples may stick to the upper jaw 30.

The cutting portion 55 of the lower jaw 50 includes a straight cutting edge 57 substantially around the outer edge of the top part 56 of the cutting portion 55. A sample receiving hole 58 is in the middle of the cutting portion 55 and is surrounded by a vertical wall 59 which has on its top part 56 the straight cutting edge 57. Along the bottom outer edge of the outside of vertical wall 59 is a groove portion 60. The groove portion 60 is configured to facilitate coupling of the pouch 16 to the lower jaw 50, for example, by receiving and retaining a protrusion on an upper part of the pouch 16.

Figure 3:
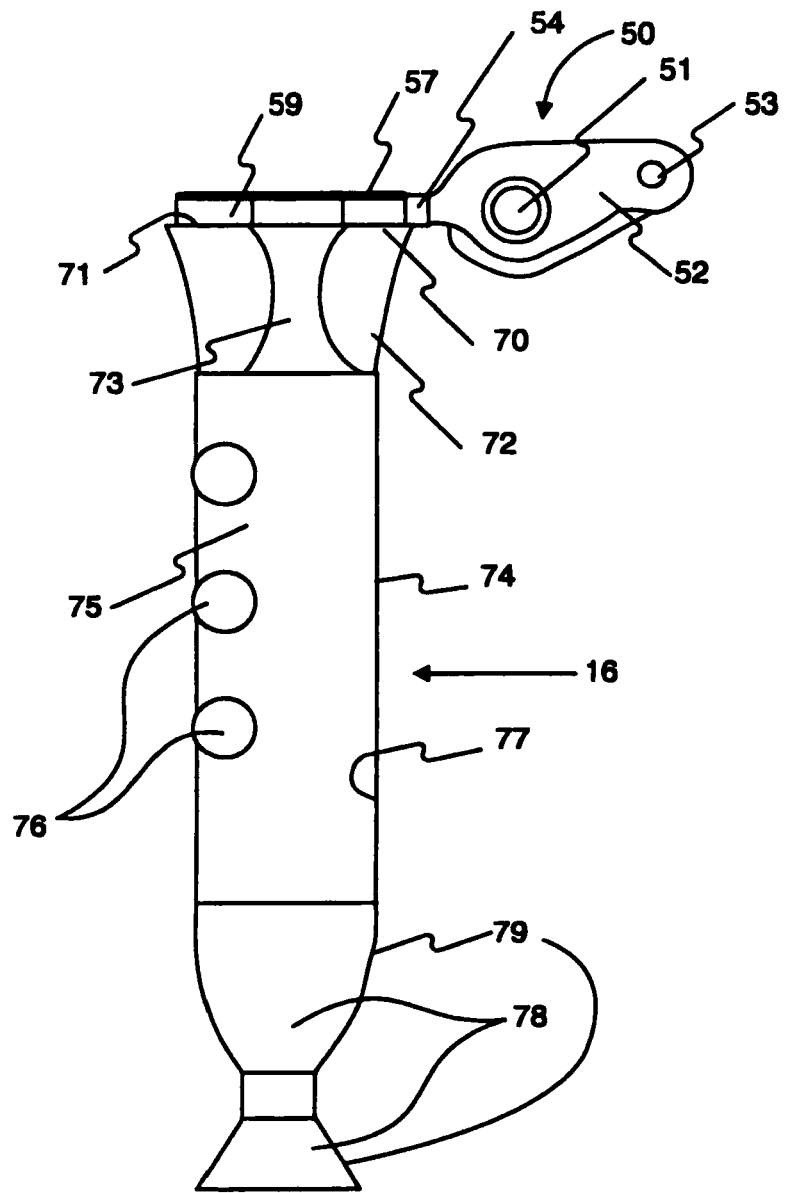
FIG. 3 is a schematic view of a collection assembly and lower jaw of the forceps and collection assembly of FIG. 1.

An embodiment of pouch 16 is depicted in FIG. 3. Pouch 16 includes a lower jaw interface portion 70, for example, an inner protrusion along its front rim 71 configured to be received and retained by the groove portion 60 of the lower jaw 50. Extending away from the front rim 71 is a base wall 72 defining a passage 73 in flow communication with the sample receiving hole 58 of the lower jaw 50. Passage 73 is configured to receiving biopsy samples from the jaws 15 through the sample receiving hole 58. Alternative configurations may include holes in the lower jaw 50 to aid in pouch attachment such as insert molding the pouch 16 directly to the jaw.

At the end of the base wall 72 opposite the front rim 71 is a pouch container 74 with a central cavity 75. The cross-section of the pouch container 74 is substantially cylindrical along its length. The central cavity 75 is in flow communication and substantially axially aligned with both the passage 73 and the sample receiving hole 58, and is configured to receive and retain the biopsy samples from the passage 73. The pouch container 74 has one or more ventilation holes 76 configured to assist in preventing the biopsy samples from sticking to the inner wall 77 of the pouch container 74, such that the biopsy samples may be more easily pushed into pouch 16 as samples are collected and removed from pouch 16 after assembly 10 is removed from a body. The ventilation holes 76 are configured to prevent such sticking by minimizing the surface area contact between the tissue samples and inner wall 77. The ventilation holes 76 are also configured to allow fluid, for example from the tissue samples, to escape from the forceps and collection pouch assembly 10.

At the bottom end of the pouch container 74 opposite the base wall 72 is a flush adapter interface 79 configured to be coupled with a flush adapter 110, to be described below. The flush adapter interface 79 has a roughly hourglass shape that defines a flush passage 78 that is open at its bottom. The flush adapter interface 79 with the flush passage 78 has a restriction that is a narrowed portion of the pouch 16. Passage 78 is configured to facilitate flow communication between the central cavity 75 of the pouch container 74 and the external environment, but prevent biopsy samples from exiting the pouch 16 through the bottom of the flush passage 78, for example, because it has a smaller cross section than the target sample sizes. The flush passage 78 and the central cavity 75 are substantially axially aligned with each other. Pouch 16 may be made of a plastic or any other suitable biocompatible material.

Figure 4:
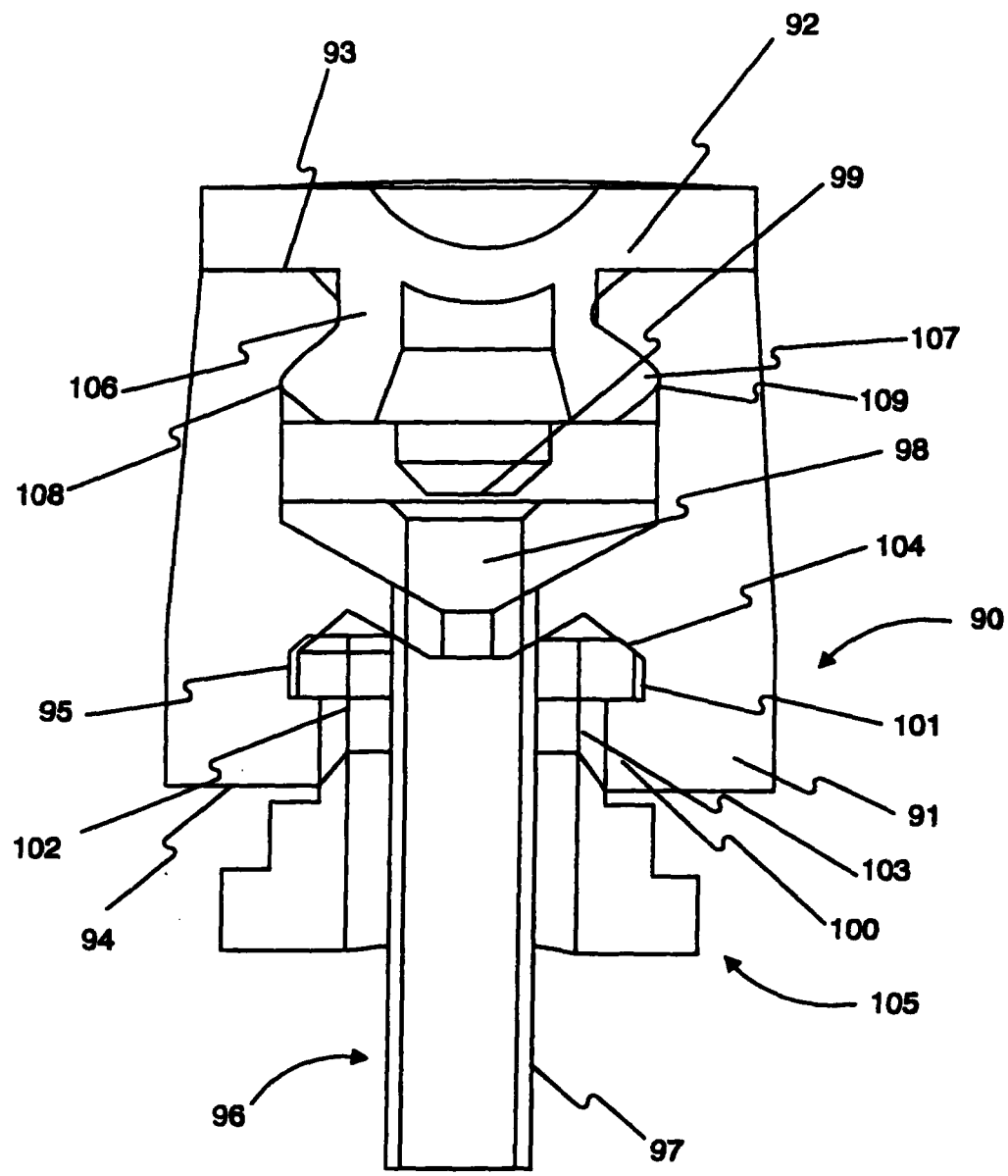
FIG. 4 is a schematic cross-sectional view of an endoscope working channel cap assembly for use with the forceps and collection assembly of FIG. 1 according to an embodiment of the present invention.

An embodiment of an endoscope working channel cap assembly 90 is depicted in FIG. 4. The cap assembly 90 includes a cap portion 91, a lid portion 92, and an introducer portion 96. The lid 92 protects the proximal end 93 of the cap 91 and is removed once the cap 91 is placed on the working channel of an endoscope and a medical instrument, for example the forceps and collection assembly 10, is advanced through the cap 91. However, in other embodiments, the lid 92 may have a central hole therethrough configured to accommodate the forceps and collection assembly 10, and thus may be left on the proximal end 93 of the cap 91 and act as a second seal. The lid 92 has a cap interface portion which includes resilient protrusions 106 with thick distal end portions 107 that bend outward. The thick distal end portions 107 of the protrusions 106 are configured to be placed in a groove 109 of a lid interface portion 108 of the cap 91 such that the lid 92 is held and retained on the cap 91 until removal by the user.

On the distal end 94 of the cap 91 is an introducer interface 95 configured to be connected to introducer 96. More specifically, interface 95 has a flange 100 and an internal groove 101 configured to receive a port fitting 105 on the proximal end of the endoscope fitting 105 has a cap interface portion 102 with a central groove 103 and a proximal protrusion 104. The port fitting 105 is configured to receive introducer 96, which has a hollow upper central shaft 98 connected to a hollow lower central shaft 97 extending distally from cap 91. The central groove 103 is configured to mate with the flange 100, while the proximal protrusion 104 is configured to mate with the internal groove 101. The lower central shaft 97 of the introducer 96 is configured to extend through and open a seal of an existing cap on the endoscope working channel and is also configured to allow the forceps and collection assembly 10 to be advanced and retracted through it, for example, by having a diameter sufficient to allow passage of the forceps and collection assembly 10.

The cap 91 itself accommodates the upper central shaft 98 of the introducer 96 configured to allow the forceps and collection assembly 10 to be advanced and retracted through it. The upper central shaft 98 is in flow communication with the lower central shaft 97 of the introducer 96. Above the upper central shaft 98 of the introducer 96, cap 91 includes a seal 99 configured to allow the forceps and collection assembly 10 to be advanced and retracted through the cap 91 via the seal 99. For example, the seal 99 may be a sheet with an X-shaped slit in the middle that is normally closed, but opens up when the forceps and collection assembly 10 extends therethrough. The seal 99 may be made of rubber or plastic and may be integrally formed with the rest of cap 91. The seal 99 is configured to substantially separate the sterile internal tissue tract environment from the non-sterile external environment both when closed and when the forceps and collection assembly 10 has been advanced through seal 99 and into the endoscope and tissue tract. In the latter situation, the seal 99 interacts with the outer portion of the tubular member 12 connected to the forceps and collection assembly 10 to effect the seal.

The seal 99 in this embodiment is different from the standard seal on a standard working channel cap known in the art, however, in that the standard seal is configured such that when the forceps and pouch assembly 10 is retracted through the seal, pouch 16 may be compressed and the biopsy samples may either fall out of pouch 16 or they may be compressed and their diagnostic integrity compromised. This may be due to the stiffness of the material comprising the standard seal and/or the geometric configuration of the standard seal.

Accordingly, seal 99 in this embodiment is configured such that the pouch 16 is not compressed to the extent in a standard seal, such that the biopsy samples are both retained in the pouch 16 while traversing the seal 99 and their diagnostic integrity is preserved. Such a lessening in compression may be obtained, for example, by making the seal 99 out of a softer or more pliable material, or by geometrically configuring the seal 99 such that less pressure is applied to the pouch 16 while it traverses the seal 99. For example, the seal 99 may be angled, may have additional central slits, or may have slits longer than the standard seal.

Figure 5A:
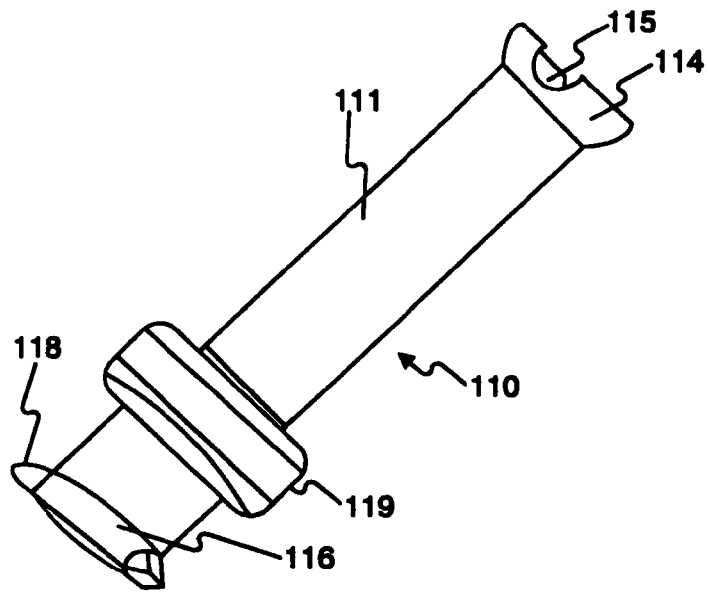
FIG. 5A is a perspective view of a flush adapter for use with the forceps and collection assembly of FIG. 1 according an embodiment of the present invention.
Figure 5B:
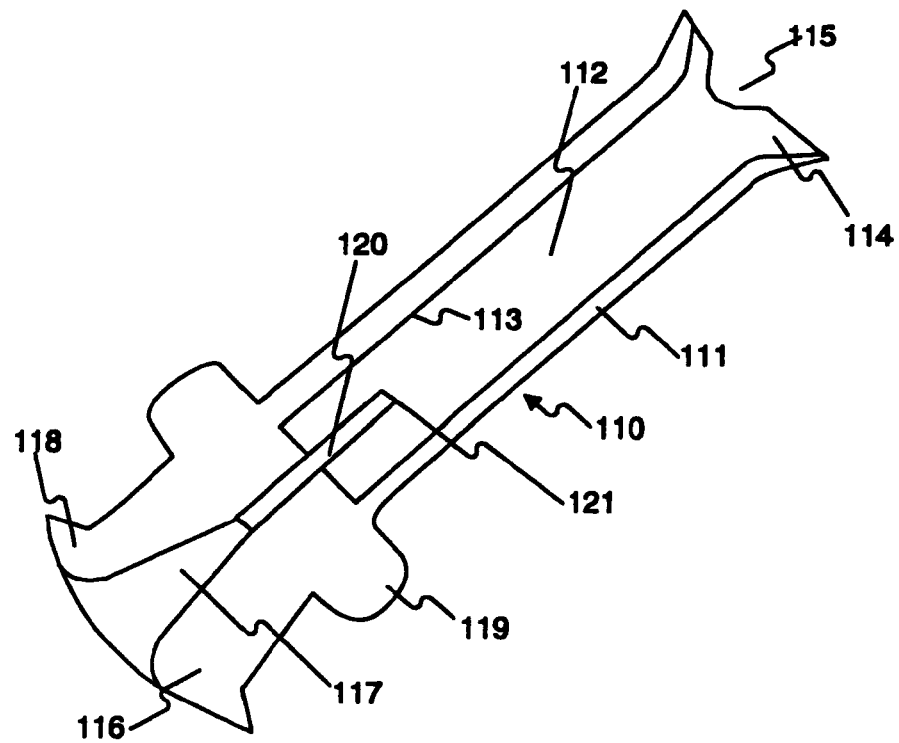
FIG. 5B is a schematic cross-sectional view of the flush adapter of FIG. 5A.

FIG. 5 depicts an embodiment of a flush adapter 110. The flush adapter 110 is configured for use with the forceps and collection assembly 10 depicted in FIGS. 1-3. The main portion of the flush adapter 110 is a cylindrical shroud 111 with a central cavity 112 that is configured to be watertight and hold the pouch 16. Accordingly, the cross-sectional area of the cylindrical shroud 111 is larger than the cross-sectional area of the pouch container 74, and may have substantially the same cross-sectional shape as the pouch container 74. The inner walls 113 of the cylindrical shroud 111 may be configured to withstand fluid pressure from the ventilation holes 76 when the pouch container 74 is placed in the cylindrical shroud 111. For example, the inner walls 113 may be dimensioned so that there is either no gap or only a very small gap between outer surface of the pouch container 74 and the inner wall 113 of the cylindrical shroud 111. Thus, even if fluid pressure were to build in the ventilation holes 76 and place pressure on the inner wall 113 of the cylindrical shroud 111, no fluid or only minimal fluid would flow between the outer surface of the pouch container 74 and the inner wall 113 of the cylindrical shroud 111.

One open end of the cylindrical shroud 111 flares out into a jaw stop 114 with notches 115 on opposites side of the jaw stop 114. That end accepts pouch 16. The flared shape of jaw stop 114 aids in guiding the pouch 16 into the cylindrical shroud 111 of the flush adapter 110, and the notches 115 are configured to receive portions of the lower jaw 50. The notches 115 also tactically indicate alignment of the forceps and pouch assembly 10 with the flush nozzle 121. For example, when portions of the lower jaw 50 are fitted into the notches 115, that indicates that the flush adapter interface 79 is aligned with and formed a substantially watertight connection with flush nozzle 121.

On the other end of the cylindrical shroud 111 of the flush adapter 110 opposite the jaw stop 114 is a luer lock 116. The luer lock 116 may be configured to fit conventional syringes. Luer lock 116 includes a funnel shaped central shaft 117 and a locking portion 118 configured to mate to a syringe or any other device capable of delivering fluid. Locking portion 118 essentially comprises an outer flange at the end of lock 116.

Between the luer lock 116 and the cylindrical shroud 111 is a support portion 119. The support portion 119 has a larger cross-sectional area than either the cylindrical shroud 111 or the luer lock 116, and is configured to, among other things, provide structural support for the flush adapter 110 and allow a user to hold the flush adapter 110. Portion 119, cylindrical shroud 111, and Luer lock 116 may be formed as an integral unit.

In the central portion of the support portion 119 is a hollow shaft 120 terminating in a flush nozzle 121. Shaft 120 may be a hypotube, part of which is lodged in the support portion 119, and part of which extends into the central cavity 112 of the cylindrical shroud 111. Hypotube 120 is configured to allow flow communication between the central shaft 117 of the luer lock 116 and the central cavity 112 of the cylindrical shroud 111. Hypotube 120 is configured to be mated with the flush adapter interface 79 of the pouch 16. The hypotube 120 is configured to be placed inside the flush passage 78 of the flush adapter interface 79. The passage 78 and hypotube 120 may be dimensioned so as to form a substantially watertight seal therebetween and/or allow fluid communication between the central shaft 117 of the luer lock 116 and the central cavity 75 of the pouch container 74.

In other embodiments, the forceps and collection assembly 10 may have various alternate configurations. For example, the clevis 17 may be any connector piece configured to couple the distal end effector assembly 11 to tubular member 12. In addition, instead of pull wires 14, assembly 10 may include any components suitable for connection to and actuation of jaws 15 or any other distal end effector assembly. Accordingly, the upper jaw 30 and lower jaw 50 need not have pull wire holes, but instead may have components configured to interface with any actuation assembly known in the art. The cutting portions 35, 55 of the upper and lower jaws 30, 50 need not be straight edge, but may have serrations, teeth, or any other cutting configuration that can cut tissue portions when brought together.

In other embodiments, pouch 16 may have various alternate configurations. For example, pouch 16 may have other shapes and may be composed of any suitable biocompatible material. The pouch 16 may be composed of a material and/or have a wall thickness that allows a desired amount of flexibility and/or compression of the pouch 16 as it traverses the seal on the cap assembly 90. For example, if the biopsy samples are especially sensitive, the pouch 16 may be configured to be more rigid such that it does not bend or compress as much when it comes into contact with either a tissue tract wall or the seal 99 on the cap assembly 90. The flush adapter interface 79 need not have an hourglass shape, as any configuration that can be coupled to the flush adapter 110 while also preventing biopsy samples from exiting the central cavity 75 through the flush adapter interface 79 is also contemplated. In addition, the pouch 16 may be integrally formed with the lower jaw 50 so that they form one piece.

In other embodiments, the cap assembly 90 may have various alternate configurations. For example, the seal 99 need not be made of rubber or plastic or integrally formed with the cap 91. Seal 99 may be separately formed and then added to the rest of cap 91, and the seal 99 may be made of any material and mechanism known in the art for separating a sterile environment from a non-sterile environment (e.g. a membrane).

In other embodiments, the flush adapter 110 may have various alternate configurations. For example, the luer lock 116 may be configured to receive the interface of any style syringe or other fluid delivery device. The jaw stop 114 need not be flared out, as it may have any configuration that assists in guiding the pouch container 74 into the cylindrical shroud 111. The jaw stop 114 need not have a notch 115, as the pouch 16 may be completely disassembled from the lower jaw 50 before being placed in the flush adapter 110. The hypotube 120 may be configured to receive a needle of a syringe, thus fluid may flow from the syringe through the needle, into the hypotube 120, out the flush nozzle 121, and into the central cavity 75 of the pouch container 74. In addition the flush adapter 110 may be configured without hypotube 120 and support portion 119, instead aligning the syringe and forceps and pouch assembly 10 so that the syringe is in direct fluid communication with the flush hole 78 of the flush adapter interface 79.

In other embodiments, the forceps and collection assembly 10 and the accompanying mechanisms described above may be used with any medical or non-medical procedure. In addition, each of the forceps and collection assembly 10, cap assembly 90, and flush adapter 110 may be used independently of the other two, each being individually configured to be used with other similar but not necessarily identical parts. For example, the cap assembly 90 may be used with any endoscopic medical instrument that may require a more sensitive and/or pliable seal 99. In another example, the flush adapter 110 may be used with any device or container that may require a coupling in order to run fluid from a fluid source to the device or container.

A method of using the forceps and collection assembly 10 and accompanying mechanisms will now be described. Once an endoscope with a working channel has been provided, the cap assembly 90 is placed on the proximal end of the working channel, typically over an existing working channel cap. Specifically, the central shaft 97 of the introducer 96 is inserted into the standard cap already on the working channel such that the central shaft 97 traverses the seal of the standard cap. Either before or after placement of cap assembly, the endoscope is placed into the body, for example, a tissue tract, using a method known in the art and the entire procedure may be viewed using any suitable method known in the art.

Once the endoscope has been placed in the desired body portion and/or tissue tract, lid 92 may be removed (although it need not be removed if it has a through hole) and a forceps and collection pouch assembly 10 is inserted through cap assembly 90, and specifically through central shaft 98 of cap 91 and shaft 97 of introducer 96, and into the working channel of the endoscope to the endoscope distal end. During insertion, the upper jaw 30 and lower jaw 50 are closed. The distal end effector assembly 11 is then advanced to the desirable tissue portion or portions and actuated. Specifically, once the jaws 15 is positioned proximate the tissue portion from which a sample is desired, the user actuates a handle portion and the jaws 15 are opened (i.e. the upper jaw 30 and lower jaw 50 are separated). For example, the pull wires 14 are advanced distally and push on the pull wire holes 33, 53 on the tang portions 32, 52. The pushing causes the tang portions 32, 53 of the upper jaw 30 and lower jaw 50 to rotate away from each other and thus cause the jaws 15 to open. The pull wires 14 may be advanced distally using any method known in the art, for example, by pushing on a spool portion of a handle.

Once jaws 30, 50 are open, the forceps and collection assembly 10 is advanced to the desired tissue and the jaws 30, 50 are closed. For example, the pull wires 14 are retracted proximally, pulling on the pull wire holes 33, 53 of the tang portions 32, 52. The pulling causes the tang portions 32, 52 to rotate toward each other and the jaws 15 to close. While the jaws 15 close, a sample of tissue is caught between the upper jaw 30 and lower jaw 50 of the jaws 15. The cutting portions 35, 55 of the upper jaw 30 and lower jaw 50 then interact and cause a biopsy sample to be cut from the tissue tract. As the jaws 15 close, the oval protrusion 38 pushes the biopsy sample into the central hole 58 of the lower jaw 50 and into the passage 73 past the front rim 71 of the pouch 16, and into the central cavity 75 of the pouch container 74. The central hole 58, the passage 73, the central cavity 75, and passage 78 and its open bottom are substantially axially aligned with each other.

Once in the central cavity 75 of the pouch container 74, the biopsy samples should fall toward the flush adapter interface end 79 of the pouch 16. However, even if they initially do not, acquisition of further samples by the jaws 15 should push the biopsy samples already in the central cavity 75 further from the front rim 71 and base wall 72. To prevent biopsy samples from getting stuck in the central cavity 75 and impeding the acquisition of further biopsy samples, the ventilation holes 76 assist in preventing such sticking by reducing the surface area on which the tissue samples can stick, thus facilitating the movement of the biopsy samples toward the flush adapter interface end 79. As the flush hole 78 is adapted to be too narrow for biopsy samples cut by the jaws 15 to pass, the biopsy samples are stored in the pouch container 74 between the flush adapter interface 79 and the front rim 71 until removal. The flush hole 78 is substantially axially aligned with the central cavity 75 of the pouch container 74.

Once the biopsy sample is stored in pouch 16, the distal end effector assembly 11 may be advanced to additional tissue tract portions where a biopsy sample may be desired, and the biopsy samples may be taken using the method substantially as set forth above. These steps may be repeated as many times as desired until either the user decides to cease acquisition of further biopsy samples or the central cavity 75 of the pouch container 74 reaches its maximum capacity.

Once the user decides that enough biopsy samples have been acquired during a single pass, assembly 10 is retracted out of the tissue tract and the working channel of the endoscope. Specifically, with jaws 15 in a closed position, forceps and collection assembly 10 is retracted back out of the endoscope working channel and cap assembly 91. During this procedure, because the seal 99 is configured to more lightly compress the pouch 16 as it traverses the seal 99 (at least as compared to a seal on a standard working channel cap), there is less risk that pouch 16 will be compressed such that either the biopsy samples are pushed out of the pouch 16 or the samples are compressed so as to compromise the diagnostic integrity of the samples.

Once the assembly 10 is retracted out of the endoscope, the biopsy samples are removed from the pouch 16. Specifically, the lower jaw 50 and pouch 16 are placed in the central cavity 112 of the cylindrical shroud 111 of the flush adapter 110 being guided by the jaw stop 114. The pouch 16 is placed almost completely in the central cavity 112 of the cylindrical shroud 111. The flush adapter interface 79 receives flush nozzle 121 such that the flush nozzle 121 is placed in the flush passage 78 of the flush adapter interface 79. The flush nozzle 121 may be lodged sufficiently in the flush passage 78 such that a substantially watertight seal is formed, and the hollow central shaft of hypotube 120 is in fluid communication with the flush passage 78. Notches 115 assist in this alignment process by tactically indicating when the jaw 50 is seated. Thus, the result is that the hypotube 120, the flush passage 78, the central cavity 75, and the passage 73 are all substantially axially aligned with each other.

Either prior to or subsequent to placing the pouch 16 in the flush adapter 110, the luer lock 116 is coupled to a syringe. Specifically, the locking portion 118 of the luer lock 116 is locked with a mating portion of the syringe such that a substantially watertight seal is formed between the syringe and the luer lock 116. Accordingly, when the pouch 16, flush adapter 110, and syringe have been properly coupled together, the syringe and central cavity 75 of the pouch 16 are in substantially watertight fluid communication via the central shaft 117 of the luer lock 116 and the hypotube 120.

Accordingly, once the pouch 16 has been placed in and coupled to the flush adapter 110, and the syringe has been coupled to the flush adapter 110, fluid is advanced out of the syringe and into the central shaft 117 of the luer lock 116. The fluid may be a sample preservation fluid, a saline solution, or any other type of desired fluid. From the syringe, the fluid flows through hypotube 120 and past flush nozzle 121 and into the central cavity 75 of the pouch container 74. In the central cavity 75 of the pouch container 74, the fluid will come into contact with the biopsy samples. The fluid then pushes the biopsy samples to the central passage 73 of the base wall 72 and then through the front rim 71. From there, the biopsy samples will be taken away for analysis or any other type of desired procedure. The endoscope may be withdrawn from the body before or after removal of samples from pouch 16.

In the various embodiments, any suitable method of viewing the procedure is contemplated, for example, the use of the endoscope lens or electronic methods of viewing endoscopic procedures that are known in the art.

In other embodiments, there may be various alternate method steps that may be executed. For example, there may not be a standard cap already on the end of the working channel of the endoscope, and the cap assembly 90 may not need an introducer 96 at all or in the form described above. Accordingly, a cap assembly 90 without an introducer may be mated with the working channel of the endoscope via the working channel interface 95 of the cap 91. As a further alternative, the upper and lower jaws 30, 50 may be individually actuated (i.e. only one jaw moves to open and close the jaws 15) and/or one jaw may be stationary and the other movable.

Figure 6D:
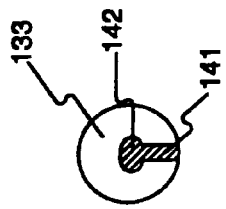
FIG. 6D is a side view of the removal mechanism of FIG. 6A.
Figure 6A:
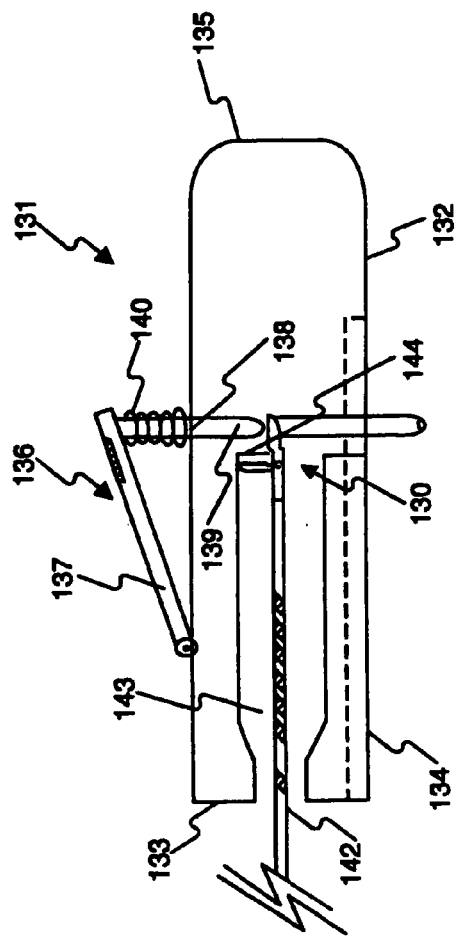
FIG. 6A is a schematic cross-sectional view of a forceps and collection assembly and a removal mechanism according to another embodiment of the present invention.
Figure 6C:
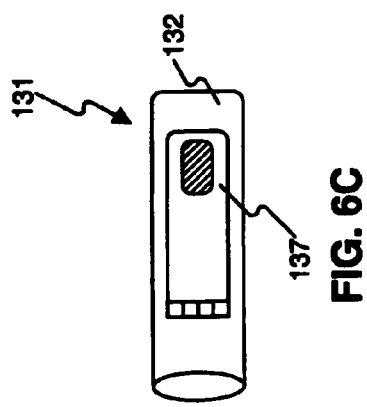
FIG. 6C is a top perspective view of the removal mechanism of FIG. 6A.

FIG. 6A depicts an alternate embodiment of a forceps and collection assembly 130. While the forceps and collection assembly 130 has upper and lower jaws with a pouch for storing multiple samples coupled to the lower jaw, there may be several differences from the embodiment depicted in FIGS. 1-3. For example, in this embodiment of forceps and collection assembly 130, the upper and lower jaw portions may be actuable about the clevis so that Accordingly, as shown in FIG. 6A, the upper jaw may be positioned at substantially a 90 degree angle with respect to the tubular member, while the lower may be substantially parallel to the tubular member such that the pouch is positioned at substantially a 90 degree angle with respect to the tubular member.

In another example, the bottom of the pouch may have a removal hole configured to prevent tissue samples from exiting the pouch via the removal hole without assistance, but allowing tissue samples to exit the pouch via the removal hole with assistance. Such a configuration can be attained, for example, by roughly determining the size of tissue samples that would be cut by the forceps jaws, and then sizing the hole to be smaller than the determined sample size, or by using a pouch like that shown in FIGS. 7A-7D.

Figure 7A:
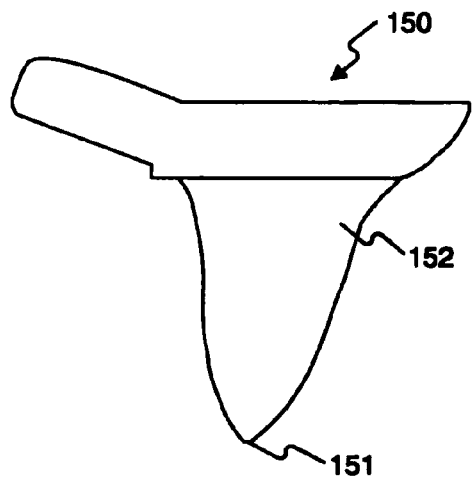
FIG. 7A is a side view of a forceps and collection assembly according to another embodiment of the present invention.
Figure 7B:
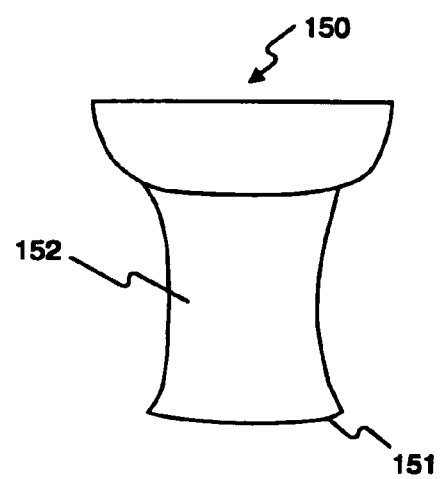
FIG. 7B is a front view of the forceps and collection assembly of FIG. 7A.
Figure 7C:
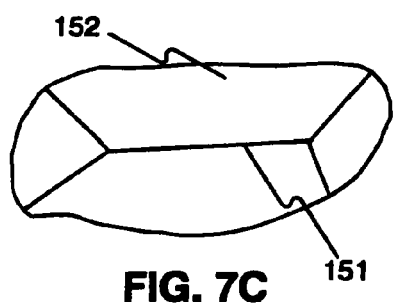
FIG. 7C is a bottom view of the forceps and collection assembly of FIG. 7A in a closed configuration.
Figure 7D:
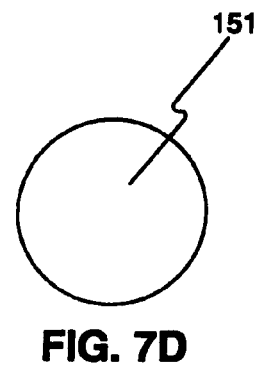
FIG. 7D is a bottom view of the forceps and collection assembly of FIG. 7A in an open configuration.

FIGS. 7A-7D depict another alternate embodiment of the forceps and collection assembly 150. While the forceps and collection assembly 150 has upper and lower jaws with a pouch for storing multiple samples coupled to the lower jaw, there may be several differences from embodiments depicted in FIGS. 1-3 and FIG. 6A. For example, the pouch of assembly 150 may have an openable and resealable bottom 151. As depicted in FIGS. 7A-7C, the pouch 152, when closed, may have a wedged shaped configuration with the bottom portion 151 having a sealing mechanism. When the bottom portion is opened, it may have a roughly circular configuration as depicted in FIG. 7D. The sealing mechanism may be a number of slits in bottom portion 151 that, due to the resilient material of pouch 152, are normally mating so that bottom 151 remains closed. When the bottom 151 is closed, the sealing mechanism may prevent tissue samples from exiting through the opening without assistance, but when either the user opens the bottom or enough external downward pressure is applied to the tissue samples, the tissue samples may be pushed or simply fall out of the pouch through the bottom opening.

FIGS. 6A-6D also depict an exemplary embodiment of a removal mechanism 131 for use, for example, with the forceps and collection assembly depicted in either FIG. 6A or FIGS. 7A-7D. The removal mechanism 131 has a cylindrical main body 132 partially open on the proximal end 133 and the bottom portion 134, and closed on the distal end 135. On the top of removal mechanism 131 is a thumb-activated plunging mechanism 136 hingeably coupled on a proximal end of an activation portion 137 to the main body 132. The activation portion 137 extends distally from the hinged portion until it roughly reaches the location of a plunger hole 138 on the main body 132. At the location of the plunger hole 138, the activation portion 137 is coupled to a plunger 139. The plunger 139 traverses the plunger hole 138 and has a return spring 140 disposed around it on the portion of the plunger 139 between the activation portion 137 and the main body 132.

Figure 6B:
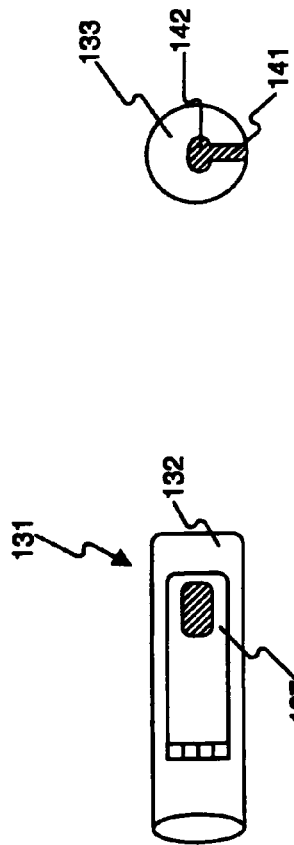
FIG. 6B is a bottom perspective of the removal mechanism of FIG. 6A.

The main body 132 has an insertion slot 141, as depicted in FIGS. 6B and 6D, configured to accommodate the forceps and collection assembly, for example, depicted in FIG. 6A or FIG. 7A-7D. The insertion slot 141 has a circular portion 142 in substantially the central part of the proximal end 133 of the main body 132, with the rest of the slot 141 extending away from the circular portion 142 until it reaches the bottom 134 of the main body 132. On the bottom 134 of the main body 132, the insertion slot 141 extends distally away from the proximal end 133, and ends roughly at the portion of the main body 132 opposite the plunger hole 138.

An embodiment of the interior of the main body 132 is depicted in FIG. 6A. Moving distally from the circular portion 142 of the insertion slot 141, the insertion slot 141 flares out into a cavity 143 which ends substantially between the plunger hole 138 and the distal end of the insertion slot 141. In the portion of the cavity 143 adjacent the plunger hole 138, there is a wall portion 144 that extends down and is configured to contact a portion of the upper jaw.

Accordingly, the forceps and collection assembly is placed in and aligned with the removal mechanism 131 such that the upper jaw contacts the wall portion 144 adjacent the plunger hole 138, and the pouch is in the insertion slot 141 with its opening directly beneath the plunger hole 138. The user then depresses the activation portion 137 such that the plunger 139 goes into the top opening of the pouch and pushes the tissue samples in the pouch out the removal hole of the pouch of FIG. 6A or the opening 151 of the pouch of FIGS. 7A-7D. The return spring 140 then returns the activation portion 137 to its original position.

Figure 8A:
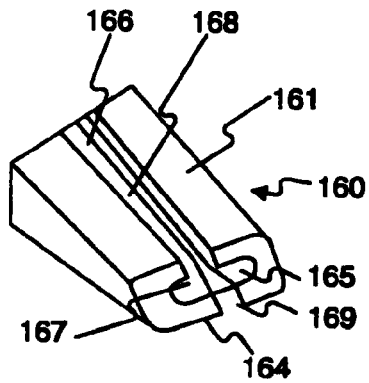
FIG. 8A is a perspective view of a removal mechanism according to yet another embodiment of the present invention.
Figure 8B:
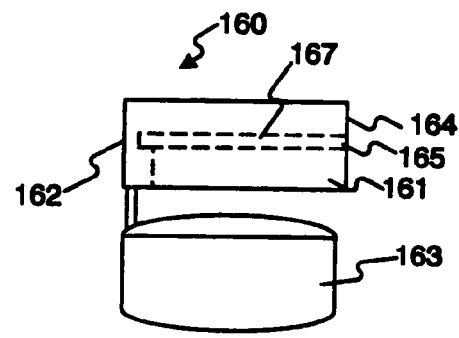
FIG. 8B is a side view of the removal mechanism of FIG. 8A.
Figure 8C:
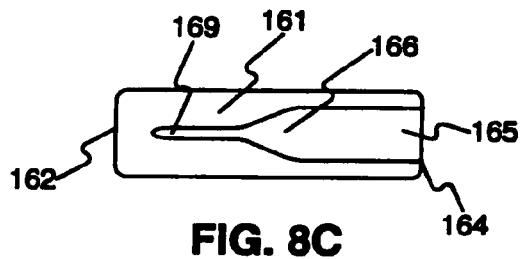
FIG. 8C is a bottom view of the removal mechanism of FIG. 8A.
Figure 8D:
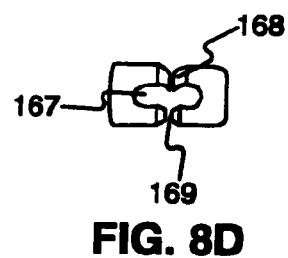
FIG. 8D is a side view of the removal mechanism of FIG. 8B.

FIGS. 8A-8D depict another exemplary embodiment of a removal mechanism 160 for use, for example, with the forceps and collection assembly depicted in either FIG. 6A or FIGS. 7A-7D. The removal mechanism 160 has a main block 161 attached at one end 162 above the open end of a fluid container 163 as depicted in FIG. 8B, and having on the other end 164 an insertion opening 165 as depicted in FIGS. 8A and 8D. The insertion opening 165 and its accompanying insertion slot 166 has a wide middle portion 167, narrower top portion 168, and narrow bottom portion 169 that run substantially the entire length of the main block 161. The width of the top 168 and middle portions 167 are substantially constant along their entire length, while the width of the bottom portion 169 narrows toward the attachment end 162, as shown in FIGS. 8C and 8D. The wide middle portion 167 is configured to receive the forceps of the forceps and collection assembly, the top portion 168 is configured to allow the traversal of the tubular member of the forceps catheter, and the bottom portion 169 is configured to accept and squeeze the pouch to facilitate the removal of the tissue samples into the fluid container.

Accordingly, in an exemplary method of using the mechanisms depicted in FIGS. 8A-8D, closed forceps jaws of a forceps and collection assembly are placed in the wide middle portion 167 of the insertion slot 165 with the tubular member extending through portion 168 and the pouch extending through portion 169 until the pouch is squeezed at its top. The user then pulls upward on the tubular member causing the forceps jaws and pouch to be pull upward and the pouch to be squeezed between the narrowing bottom portions 169 of the insertion slot 165. This squeezing causes the tissue samples to fall out of the bottom of the pouch and into the fluid container 163.

Figure 9A:
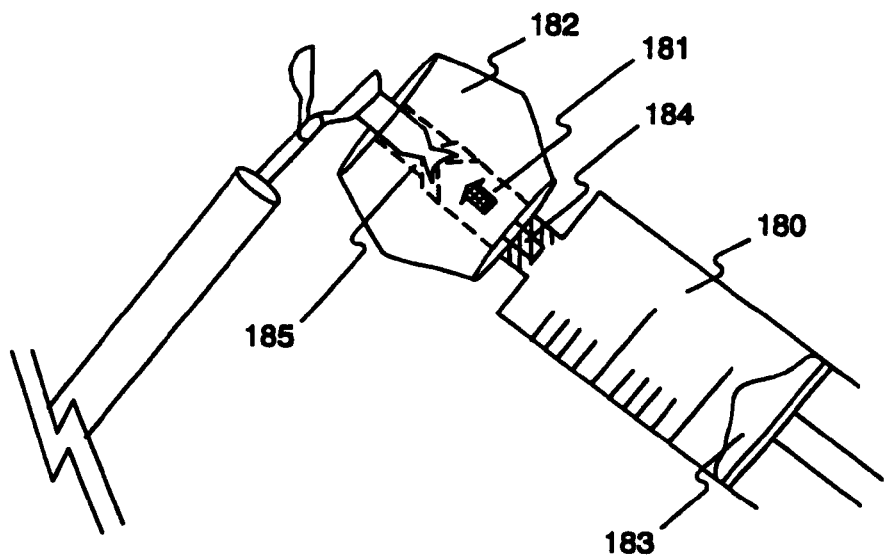
FIG. 9A is a perspective view of the forceps and collection assembly of FIG. 1 being used in conjunction with a flush adapter according to still another embodiment of the present invention.
Figure 9B:
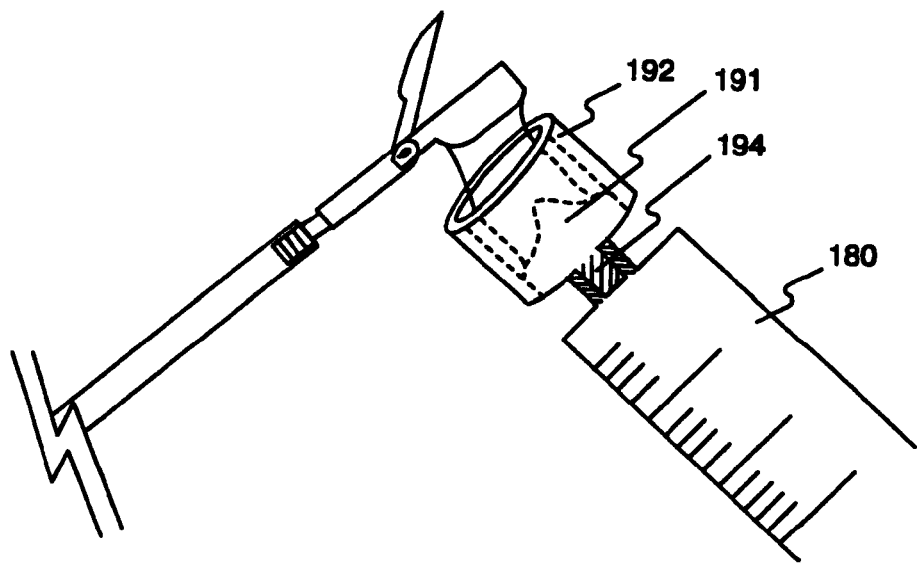
FIG. 9B is a perspective view of the forceps and collection assembly of FIG. 1 being used in conjunction with a flush adapter according to a further embodiment of the present invention.

FIGS. 9A and 9B depict alternate embodiments of a flush adapter being used in conjunction with the forceps and collection assembly of FIG. 1-3. FIG. 9A shows a flush adapter having a housing portion 182 with an internal nozzle 181 and a pouch cavity 185. A syringe 180, with a plunger 183, is placed in fluid communication with nozzle 181, which is substantially cone shaped, and cavity 185. Cavity 185 is configured to receive a pouch of a forceps and collection assembly, for example, of FIG. 1-3. Housing 182 also includes a male luer lock 184 to be received by a female luer lock of the syringe. Fluid flows from the syringe 180, through the nozzle 181, and into the pouch placed in cavity 185.

In another example, the flush adapter of FIG. 9B is similar to the embodiment of FIG. 9A in that it has a housing portion 192 with a nozzle 191 and a male luer lock 194. In this embodiment, nozzle 191 has a parabolic taper.

Figure 10A:
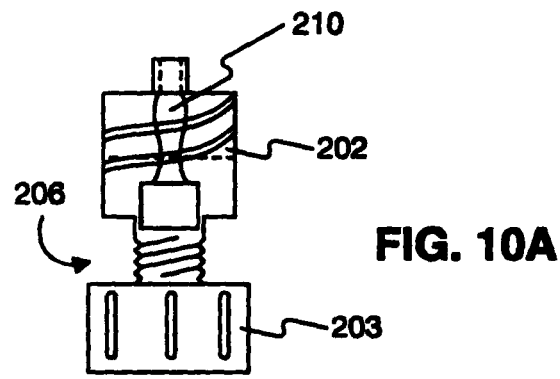
FIG. 10A is a side view of the forceps and collection assembly of FIG. 1 being used in conjunction with a portion of a flush adapter according to a still further embodiment of the present invention.
Figure 10B:
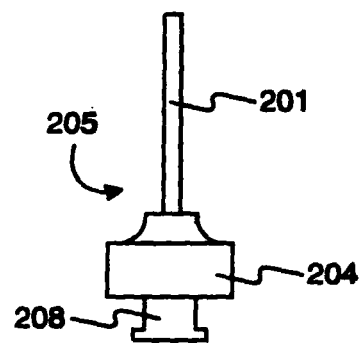
FIG. 10B is a side view of another portion of the flush adapter of FIG. 10A.
Figure 10C:
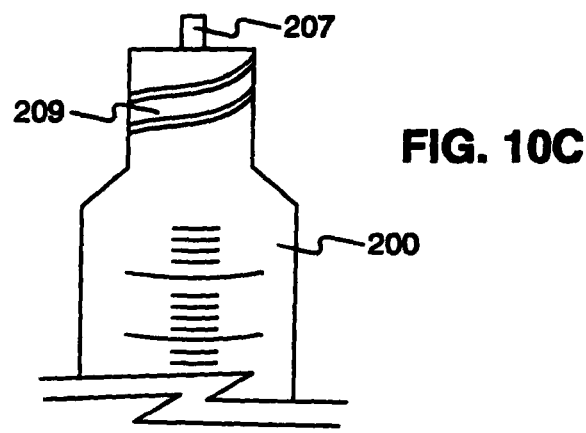
FIG. 10C is a side view a syringe for use with the flusher adapter of FIGS. 10A and 10B.

FIGS. 10A-10C depict another alternate embodiment of a flush adapter that may be used in conjunction with the forceps and collection assembly of FIG. 1-3. The flush adapter is similar to the flush adapters of FIGS. 9A and 9B, but differs in certain aspects. In this embodiment, a syringe 200 is coupled to an intermediate portion 205 through a luer connection. The syringe 200 has a male luer lock 207 configured to be coupled and in fluid communication with the female luer lock 208 of the intermediate portion 205. The intermediate portion 205 has a hypotube 201 with a nozzle on one end and a housing mating portion 204 configured to mate with a mating portion 203 of a housing portion 206. The syringe 200 also has a housing mating portion 209 configured to be coupled to the mating portion 203 of the housing portion 206. The mating portion 203 is screwed onto a pouch accommodating portion 202 configured to receive the forceps and collection assembly, for example, of FIGS. 1-3. Accordingly, fluid from the syringe 200 is run through the hypotube 201 of the intermediate flushing device 205, out the nozzle portion, and into the pouch 210 which is lodged in the pouch accommodating portion 202 of the housing portion 206.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A medical device comprising:
a first jaw and a second jaw pivotably connected to the first jaw;
wherein the first jaw includes an elongate container having a cavity for storing a plurality of tissue samples, an open top, and a bottom in communication with the open top;
wherein the first jaw includes a cutting portion coupled to the open top and configured to cut the plurality of tissue samples that deposit in the cavity through the open top,
wherein a portion of the container adjacent the bottom is normally closed to prevent the plurality of tissue samples from exiting the container via the bottom, and wherein the portion of the container is configured to open.
2. The medical device of claim 1, wherein the portion of the container includes slits therein.
3. The medical device of claim 2, wherein the portion of the container has a wedge shape when normally closed.
4. The medical device of claim 2, wherein the portion of the container defines a through hole in communication with the bottom when the portion of the container is open.
5. The medical device of claim 2, further comprising a flushing device that is configured to mate with the elongate container, the flushing device being configured to move the portion of the container from normally closed to open to facilitate removal of the plurality of tissue samples.
6. The medical device of claim 1, wherein the container is formed of resilient material, and wherein the portion of the container includes a plurality of flaps biased to seal the bottom.
7. A medical device comprising:
a first jaw and a second jaw pivotably connected to the first jaw;
wherein the first jaw includes an elongate container having a cavity for storing a plurality of tissue samples, an open top, and a bottom in communication with the open top; and wherein the first jaw includes a cutting portion coupled to the open top and configured to cut the plurality of tissue samples that deposit in the cavity through the open top;

a sealing mechanism disposed adjacent the bottom, the sealing mechanism being movable between a closed configuration and an open configuration, wherein, in the closed configuration, the sealing mechanism is configured to prevent tissue samples from exiting the container via the bottom.

8. The medical device of claim 7, wherein the sealing mechanism includes a plurality of flaps.

9. The medical device of claim 8, wherein the plurality of flaps mate so as to seal the bottom in the closed configuration.

10. The medical device of claim 8, wherein the plurality of flaps are biased to the closed configuration.

11. The medical device of claim 8, wherein the container is formed of resilient material, and wherein the plurality of flaps are separated from each other by slits in the resilient material.

12. The medical device of claim 8, wherein the plurality of flaps include at least three flaps.

13. A medical device comprising:

a first jaw and a second jaw pivotably connected to the first jaw;

wherein the first jaw includes an elongate container, wherein the elongate container has a cavity for storing a plurality of tissue samples and an open top;

wherein the first jaw includes a cutting portion coupled to the open top and configured to cut the plurality of tissue samples that deposit in the cavity through the open top, and wherein the elongate container has a sealable opening configured to prevent the tissue samples from exiting a bottom of the cavity.

14. The medical device of claim 13, wherein the sealable opening and the open top are aligned on a longitudinal axis of the cavity.

15. The medical device of claim 13, wherein a portion of the container adjacent the sealable opening includes at least three flaps.

16. The medical device of claim 15, wherein the at least three flaps are biased to contact each other and close the sealable opening.

17. The medical device of claim 15, wherein the at least three flaps are configured to move between a closed configuration in which the sealable opening is closed and an open configuration in which the sealable opening is open to facilitate removal of the tissue samples.

18. The medical device of claim 17, wherein, when the at least three flaps are in the closed configuration, a bottom portion of the elongate container has a tapered shape.

19. The medical device of claim 17, wherein, when the at least three flaps are in the open configuration, the elongate container has a cylindrical shape.

* * * * *